US006854972B1

(12) United States Patent
Elian

(10) Patent No.: US 6,854,972 B1
(45) Date of Patent: Feb. 15, 2005

(54) DENTAL IMPLANTS AND DENTAL IMPLANT/PROSTHETIC TOOTH SYSTEMS

(76) Inventor: Nicholas Elian, 110 Bleecker St., New York, NY (US) 10012

( * ) Notice: Subject to any disclaimer, the term of this patent is extended or adjusted under 35 U.S.C. 154(b) by 0 days.

(21) Appl. No.: 09/481,212

(22) Filed: Jan. 11, 2000

(51) Int. Cl.[7] .............................................. A61C 8/00
(52) U.S. Cl. ...................................... 433/173; 433/174
(58) Field of Search ................................ 433/173, 174, 433/175, 176

(56) References Cited

U.S. PATENT DOCUMENTS

| | | |
|---|---|---|
| 3,905,109 A | 9/1975 | Cohen et al. |
| 4,334,865 A | 6/1982 | Borle |
| 4,468,200 A | 8/1984 | Münch |
| D296,362 S | 6/1988 | Branemark |
| 4,832,601 A | 5/1989 | Linden |
| 4,872,839 A | 10/1989 | Brajnovic |

(List continued on next page.)

FOREIGN PATENT DOCUMENTS

EP          0 868 889       10/1998

OTHER PUBLICATIONS

Esposito, Marco, DD S. Ph D, et al., "Histopathologic Observations on Early Oral Implant Failures", The International Journal of Oral Maxillofacial Implants 1999; vol. 14, pp. 798–810.
Kohal, Ralf–J., DMD, et al., "Clinical and Histologic Evaluation of Submerged and Non–submerged Hydroxyapatite–Coated Implants: A Preliminary Study of Dogs", The International Journal of Oral Maxillofacial Implants 1999, vol. 14, pp. 824–834.

Esposito, M., et al., "Biological Factors Contributing to Failures of Osseointegrated Oral Implants (I).Success Criteria and Epidemiology", Eur. J. Oral Sciences 1998; vol. 106, pp. 527–551.
Esposito, M., et al., "Biological Factors Contributing to Failures of Osseointegrated Oral Implants (II). Etiopathogenesis", Eur. J. Oral Sciences 1998, vol. 106, pp. 721–764.
Cochran, David L., et al., "Biologic Width Around Titanium Implants. A Histometric Analysis of the Implanto–Gingival Junction Around Unloaded and Loaded Nonsubmerged Implants in the Canine Mandible", J. Periodontol 1997; vol. 68, pp. 186–198.

*Primary Examiner*—Nicholas D. Lucchesi
(74) *Attorney, Agent, or Firm*—Morgan & Finnegan, LLP

(57) ABSTRACT

A one-piece dental implant having a longitudinal axis comprises a head portion at a first end of the implant, a tip portion at a second end of the implant and a body portion between the head portion and the tip portion. The body portion has a first portion proximate the head portion with a plurality of longitudinal grooves substantially parallel to the longitudinal axis and a second portion proximate the tip portion having a substantially circumferential groove, wherein the outer diameter of the first portion is greater than the outer diameter of the second portion. The first and second portions are for being embedded in the jaw bone. The dental implant is preferably dimensioned to conform to the natural shape of the cervical ⅓ of the root of the tooth being replaced, and to the natural relationship between the cemento-enamel junction of the tooth being replaced and to minimize adverse immunological responses by the jaw bone during healing, thereby improving the aesthetic appearance of the implant and prosthetic tooth attached thereto. A dental implant and prosthetic tooth system is also disclosed, wherein the prosthetic tooth conforms to the shape of the cervical ⅓ of the crown of the tooth being replaced. A method for implanting a dental implant through use of a reference, is also disclosed.

47 Claims, 18 Drawing Sheets

U.S. PATENT DOCUMENTS

| | | | | |
|---|---|---|---|---|
| 5,061,181 A | | 10/1991 | Niznick | |
| 5,073,111 A | | 12/1991 | Daftary | |
| 5,145,371 A | | 9/1992 | Jörnéus | |
| 5,176,709 A | | 1/1993 | Branemark | |
| 5,195,892 A | | 3/1993 | Gersberg | |
| 5,312,254 A | | 5/1994 | Rosenlicht | |
| 5,312,256 A | | 5/1994 | Scortecci | |
| 5,316,476 A | | 5/1994 | Krauser | |
| 5,338,197 A | | 8/1994 | Kwan | |
| 5,362,236 A | * | 11/1994 | Branemark | 433/173 |
| D356,868 S | | 3/1995 | Broberg et al. | |
| 5,417,568 A | * | 5/1995 | Giglio | 433/173 |
| 5,427,527 A | | 6/1995 | Niznick et al. | |
| 5,431,567 A | | 7/1995 | Daftary | |
| 5,533,898 A | | 7/1996 | Mena | |
| 5,642,996 A | | 7/1997 | Mochida et al. | |
| 5,674,069 A | | 10/1997 | Osorio | |
| 5,681,167 A | | 10/1997 | Lazarof | |
| 5,759,034 A | | 6/1998 | Daftary | |
| 5,759,036 A | | 6/1998 | Hinds | |
| 5,772,437 A | | 6/1998 | Rangert et al. | |
| 5,779,480 A | | 7/1998 | Groll et al. | |
| 5,810,592 A | | 9/1998 | Daftary | |
| 5,824,079 A | | 10/1998 | Siegler et al. | |
| 5,863,201 A | | 1/1999 | Lazzara et al. | |
| 6,164,969 A | * | 12/2000 | Dinkelacker | 433/173 |
| 6,174,167 B1 | | 1/2001 | Wohrle | |
| 6,217,333 B1 | * | 4/2001 | Ercoli | 433/173 |
| 6,375,465 B1 | * | 4/2002 | Engman et al. | 433/173 |

* cited by examiner

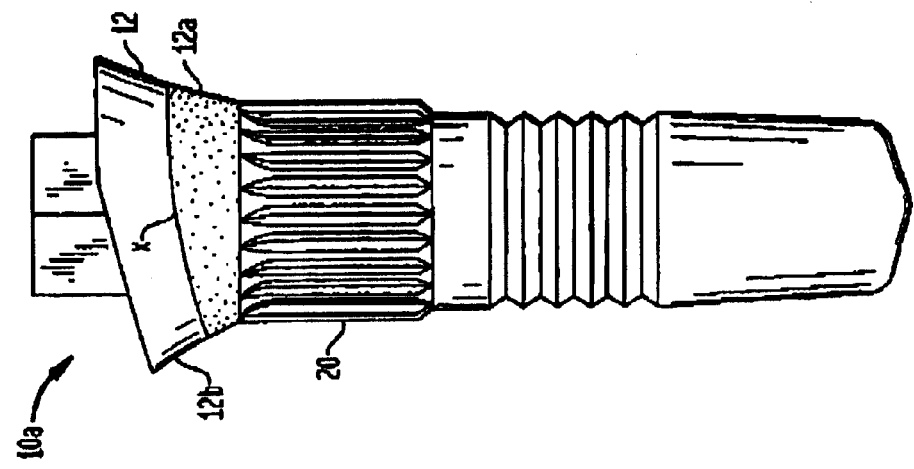
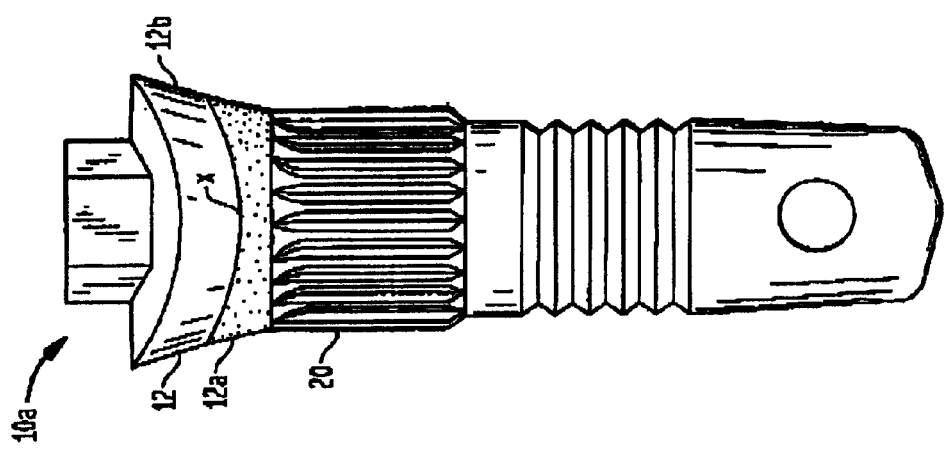

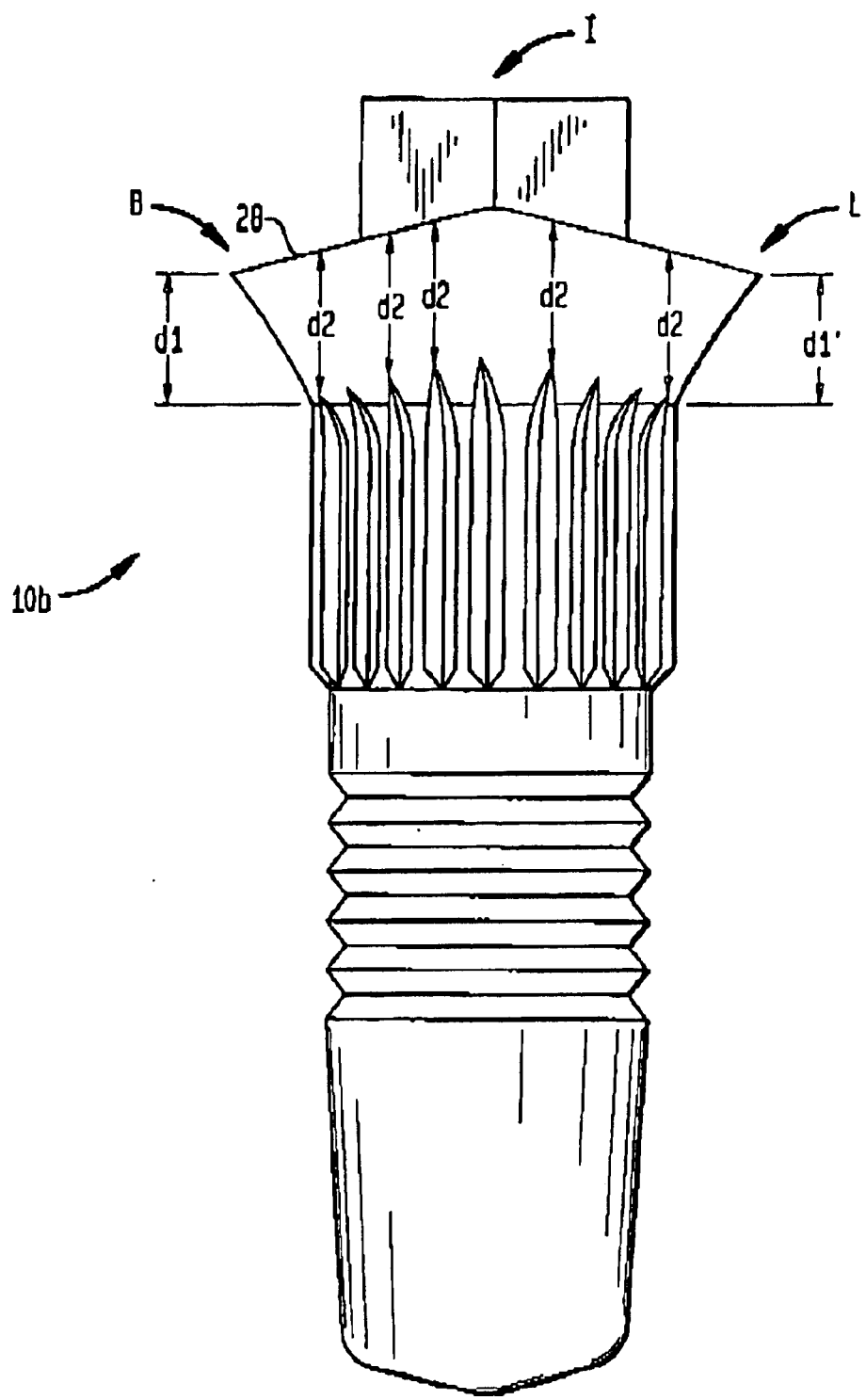

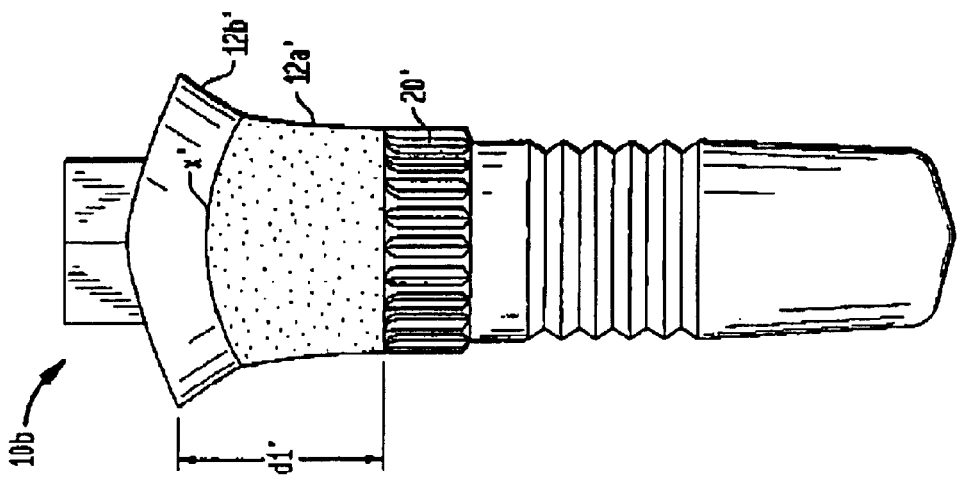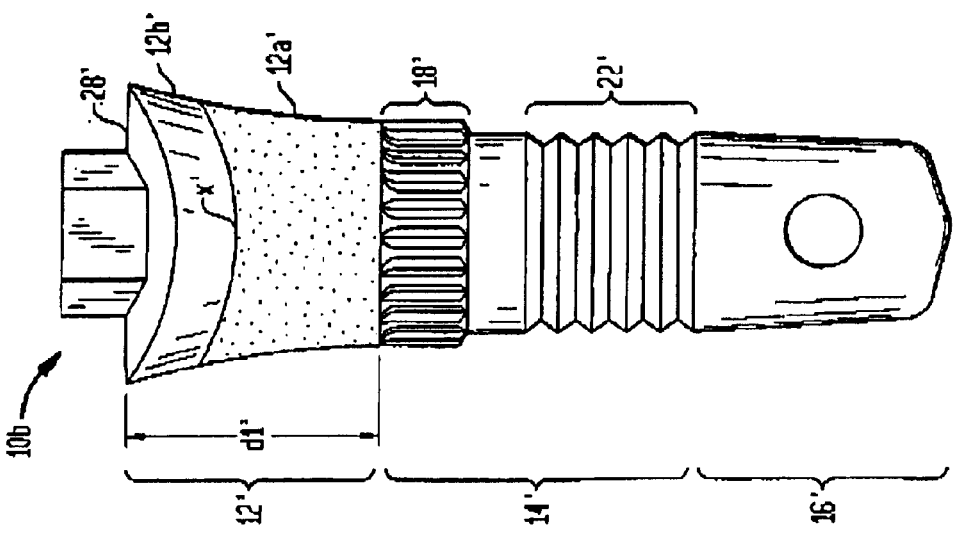

DENTAL IMPLANTS AND DENTAL IMPLANT/PROSTHETIC TOOTH SYSTEMS

BACKGROUND OF THE INVENTION

Dental implants are inserted into the base of the jaw and have a portion protruding through the mucous gum tissue for providing attachment anchorage for artificial teeth. An artificial tooth may be attached directly to the implant, or to an abutment connected to the implant. Dental implants are becoming increasingly popular alternatives to dentures.

Dental implants have been used in the hard bone of the lower jaw with great success. The upper jaw bone, however, is very soft and it is common for dental implants in the upper jaw to lack primary stability.

There are three major types of dental implants: 1) press-fit; 2) self-tapping; and 3) pre-tapping. The press-fit type implants are inserted into holes drilled into the bone without rotation. Press-fit implants do not couple tightly to the soft bone of the upper jaw.

Self-tapping and pre-tapping type implants have horizontal threads for being screwed into holes drilled into the jaw-bone, for better mechanical coupling to the jaw bone. Self-tapping implants create grooves in the hole as the implant is screwed in. Prior to the insertion of pre-tapped implants, a tool is used to form threads in the hole. While screwing self-tapping and pretapping implants into the bone generally improves the mechanical coupling between the implant and bone, it has been found that in the soft bone of the upper jaw, the rotation of both the self-tapping and pre-tapping implants may destroy the grooves, preventing tight coupling between the implant and the bone.

After insertion of the implant, a sufficient period of time must be given for the tissue to heal and for the bone to grow sufficiently around (and sometimes through) the implant for the dental implant to become securely engaged in the jaw. This typically requires about three months. An artificial tooth is then attached to the implant, directly or by attachment to an abutment attached to the implant.

Primary stability, osteointegration and the aesthetic appearance of the implant and prosthetic tooth in the mouth are important considerations in the design of a dental implant. Mechanical solutions to achieving primary stability and osteointegration have generally ignored the natural shapes of the root and crown of the natural tooth being replaced and have not conformed to the natural relationship between the tooth and the jaw bone, resulting in adverse immunological responses by the jaw bone which both weakens primary stability and osteointegration, and sacrifices aesthetics.

FIG. 1 shows two adjacent natural adult teeth 100, in the upper jaw. A tooth 100 has a crown and a root. The crown may be divided into a cervical ⅓, a middle ⅓ and an incisal ⅓. The root may be divided into a cervical ⅓, a middle ⅓ and an apical ⅓. The interface between the cervical ⅓ of the tooth and the cervical ⅓ of the root is referred to as the cemento-enamel junction. It has been observed that in a natural tooth, the distance d3 between the cemento-enamel junction 104 and the crest 102 of the jaw bone is typically about 1.8 mm and the distance d4 between the crest 102 of the jaw bone and the gingival margin 108 is typically about 3 mm.

Adverse immunological responses may be caused by a variety of stimuli. For example, it has been found that the failure of interface between the dental implant and the prosthetic tooth to conform to the shape and location of the cemento-enamel junction between the crown and root of the tooth being replaced causes an adverse immunological response by the bone to the dental implant, resulting in bone resorbtion. This can weaken the bond between the implant and the bone and leave pockets which can collect plaque. In addition, since a constant distance is naturally maintained between the bone crest and the gingival margin, as the bone resorbs, the gingival margin recesses, presenting an unpleasant aesthetic appearance.

Another cause of adverse immunological responses in the jawbone are microgaps between the dental implant, whose top surface is typically positioned at or below the bone crest, and the abutment attached to the implant. Once again, bone resorbtion and gingival margin recession may result.

Some dental implants, such as the ITI(R) implants from the Straumann Company, Waltham, Mass., position the top surface of the implant above the bone crest. The jaw bone is not, therefore, exposed to microgaps between the implant and an abutment, decreasing adverse immunological responses. However, the flat tops of these implants do not match the shape of the cemento-enamel junction of the natural tooth being replaced. Bone resorbtion and the resulting recession of the gingival margin still occur, particularly interproximally.

Dental implants are also typically cylindrical. However, teeth are not so regularly shaped. While attempts have been made to conform the abutment and the prosthetic tooth to the natural shape of the cervical ⅓ of the root and the cervical ⅓ of the crown of the tooth being replaced, the unnatural shape of the dental implant limits how closely the natural shape of the root and crown can be recreated. Voids are therefore present between the dental implant and the bone of the jaw, and between the prosthetic tooth and the gingivus, which can allow for the growth of soft tissue and the collection of plaque. Such soft tissue may interfere with the osteointegration of the implant, resulting in implant failure. Attempts have been made to prevent soft tissue growth by filling the gaps between the implant and the jaw bone by artificial bone or by covering the interface between the gums and the implant with a membrane. Such designs have an increased risk of infection and lack osteointegration. Rotation of the implant, either during rotation of the implant to insert the implant into the jaw bone or after final positioning of the implant, also interferes with attempts to close such gaps.

SUMMARY OF THE INVENTION

In one aspect of the invention, a dental implant has both longitudinal and vertical grooves for improved primary stability and osteointegration. In other aspects of the invention, a dental implant and a dental implant/prosthetic tooth system substantially conforms to the natural relationships and shapes of the tooth being replaced. In particular, a dental implant is shaped and dimensioned to substantially conform to the natural biological relationship between the bone crest and the cemento-enamel junction. The gingival margin is therefore maintained. The preferred dental implant combines these aspects of the invention.

A one-piece dental implant is disclosed having a longitudinal axis comprising a head portion at a first end of the implant, a tip portion at a second end of the implant and a body portion between the head portion and the tip portion. The body portion has a first portion proximate the head portion with at least one longitudinal groove substantially parallel to the longitudinal axis and a second portion proximate the tip portion having a substantially circumferential groove or threads. Preferably, a plurality of longitudinal grooves are provided. The outer diameter of the first portion is greater than the outer diameter of the second portion. The first and second portions are embedded in the jaw bone. The longitudinal grooves of the implant are received in longitudinal grooves formed in the opening made in the jaw bone for receiving the implant, preventing rotation of the implant during placement and healing. During healing, the jaw bone grows into the circumferential groove, securing the implant in the jaw bone. The circumferential groove may be a spiral thread which circles the body portion a plurality of times, or a plurality of parallel grooves substantially perpendicular to the longitudinal axis.

In another embodiment of the embodiment of the invention, a dental implant is disclosed having a head portion. The head portion has a top surface with a circumference substantially matching the circumference of the tooth to be replaced, at the cemento-enamel junction of the tooth being replaced.

In another embodiment of the embodiment of the invention, a dental implant is provided having a buccal side for being aligned with the buccal side of the jaw bone, a lingual side for being aligned with a lingual side of the jaw bone and interproximal sides between the buccal and lingual sides. The height of the top portion of the dental implant is less on the buccal side of the implant and rises toward the interproximal sides of the implant, as does the cemento-enamel junction. The height of the top portion may decrease from the interproximal sides of the implant to the lingual side, as well.

In another embodiment of the invention, a dental implant and prosthetic tooth system is disclosed, wherein the height of the top portion of the dental implant is less on the buccal side of the implant and rises toward the interproximal sides of the implant. The prosthetic tooth has a portion having a shape substantially matching the shape of the cervical ⅓ of the crown of the tooth being replaced. The height of the top portion may decrease from the interproximal sides of the implant to the lingual side.

In another embodiment of the invention, a dental implant and prosthetic tooth system is disclosed comprising a dental implant having a head portion, a tip portion and a body portion between the head portion and the tip portion. The head portion has a top surface with a circumference substantially matching the circumference of the tooth being replaced, at about the cemento-enamel junction of the tooth being replaced. A prosthetic tooth for being attached to the top surface of the implant has a shape substantially matching the shape of the cervical ⅓ of the tooth being replaced.

In another embodiment of the invention, a method of implanting a dental implant is disclosed wherein a reference provided on the implant is used to properly position the implant in the jaw bone. The reference can be defined by the ends of longitudinal grooves extending into the head of the implant, or by the end of the surface treated portion of the head of the implant, which is positioned at or slightly below the bone crest. Preferably, the head portion of the implant is positioned above the bone crest after implantation.

BRIEF DESCRIPTION OF THE DRAWINGS

FIGS. 4a and 4b are side views of the buccal side and proximal side of an alternative configuration for the dental implant of the present invention.

FIG. 9 is a side view of the proximal side of another implant in accordance with the present invention;

FIGS. 11a and 11b are side views of the buccal and proximal sides, respectively, of a dental implant with a head portion which is longer than in the configuration of FIGS. 4a and 4b.

DETAILED DESCRIPTION OF THE INVENTION

Figure 1:
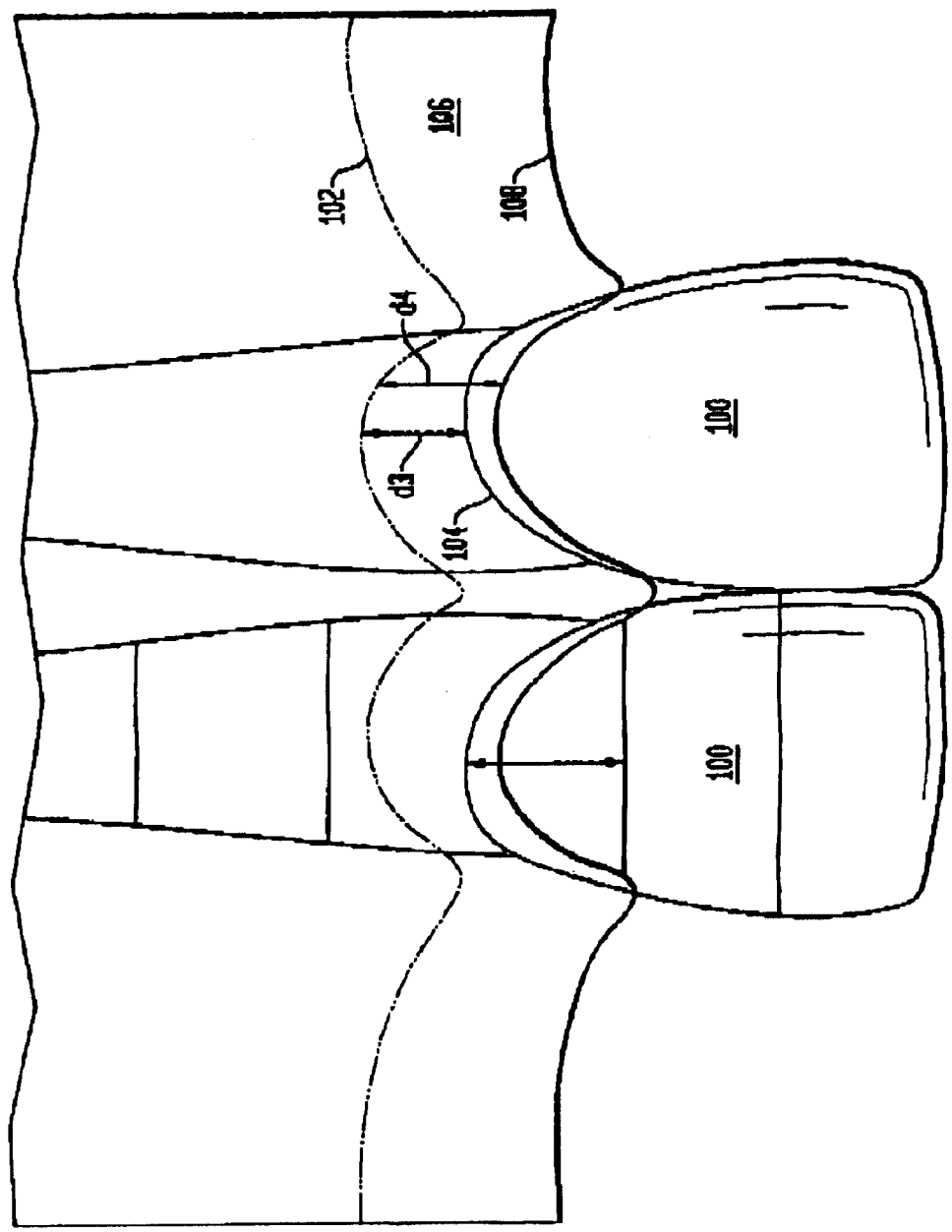
FIG. 1 is a view of two adjacent teeth of the upper jaw.
Figure 3:
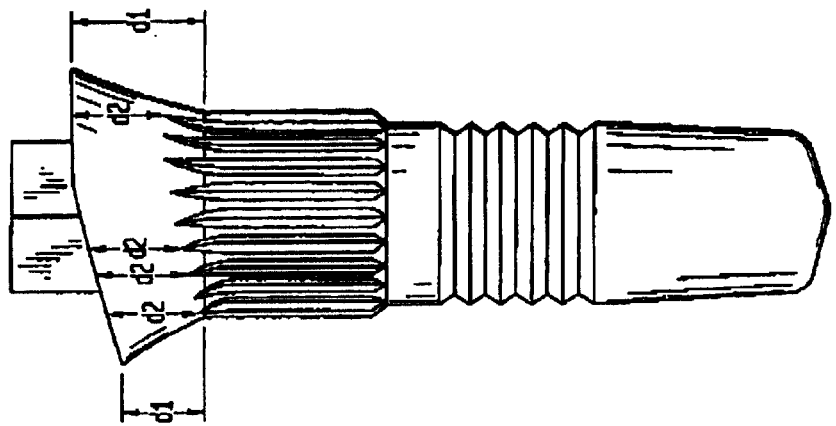
FIG. 3 is a side view of the proximal side of the dental implant of FIG. 1.
Figure 2:
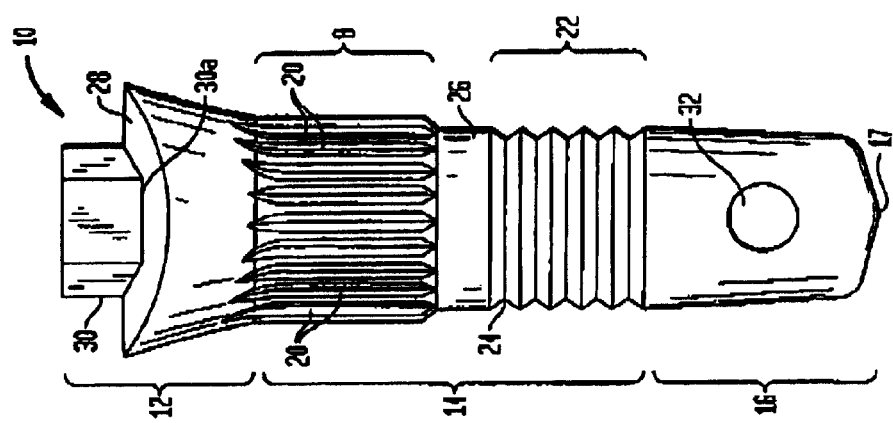
FIG. 2 is a side view of the buccal side of a dental implant in accordance with one embodiment of the present invention.

FIG. 2 is a side view of the buccal side of a dental implant 10 in accordance with one embodiment of the present invention. FIG. 3 is a side view of the proximal side of the dental implant 10 of FIG. 2. The dental implant 10 is preferably a single piece with a head portion 12, a body portion 14 and a tip portion 16, extending along a longitudinal axis "L".

The body portion is cylindrical and includes a first section 18 with a plurality of longitudinal grooves 20 substantially parallel to the longitudinal axis L of the implant 10, proximate the head portion 12. Preferably, at least some of the longitudinal grooves 20 extend into the head portion 12. The depth of each groove 20 may be about 1 mm. The outer diameter of the first section is preferably from about 3.75 mm to about 5.00 mm depending on the type of tooth being replaced and the position of the tooth in the mouth.

The cylindrical body portion 14 includes a second section 22 with a circumferential spiral thread 24. Preferably, the spiral thread 24 encircles the second section 22 of the body portion 14a plurality of times. Alternatively, a plurality of parallel circumferential grooves can be provided. Such parallel grooves can be perpendicular to the longitudinal axis L of the implant or they may be at a slight angle from perpendicular. The circumferential thread 24 or grooves may be rough or serrated. The outer diameter of the horizontal thread 24 or grooves of the second section 22 is less than the outer diameter of the vertical grooves 20 of the first section 18.

A narrow flat walled section 26 is preferably provided between the first section 18 and the second section 22 to separate the first and second sections, easing manufacture of the implant 10. The outer diameter of the flat walled section 26 is preferably about the same as the outer diameter of the second section 22.

The head portion 12 has an outwardly flaring side wall and a top surface 28 including a hex 30 for attachment of an artificial tooth. The edge 30a between the top surface 28 and the hex 30 preferably has a chamfer-like finish so that the edge 30a is curved. An internal hex may also be provided through the top surface of the implant, as is known in the art. Other attachment mechanisms may be used, as well. The portion of the head portion 12 between the longitudinal grooves and the top surface 28 is preferably polished to provide a smooth surface which inhibits the collection of bacteria.

The extent of the outward flare of the head portion 12 is sufficient to close the opening formed in the jaw bone for receiving the implant, as described further, below. In addition, the shape of the side wall of the head portion 12 preferably substantially matches the shape of the cervical ⅓ of the root of the natural tooth being replaced. The shape of the root of the natural tooth may be determined through a CAT and clinical measurements scan prior to extraction of the tooth, as is known in the art. If the natural tooth is not present, then the shape of the root may be approximated by analysis of adjacent teeth by CAT scan and/or clinical measurements, which is also known in the art.

Figure 8:
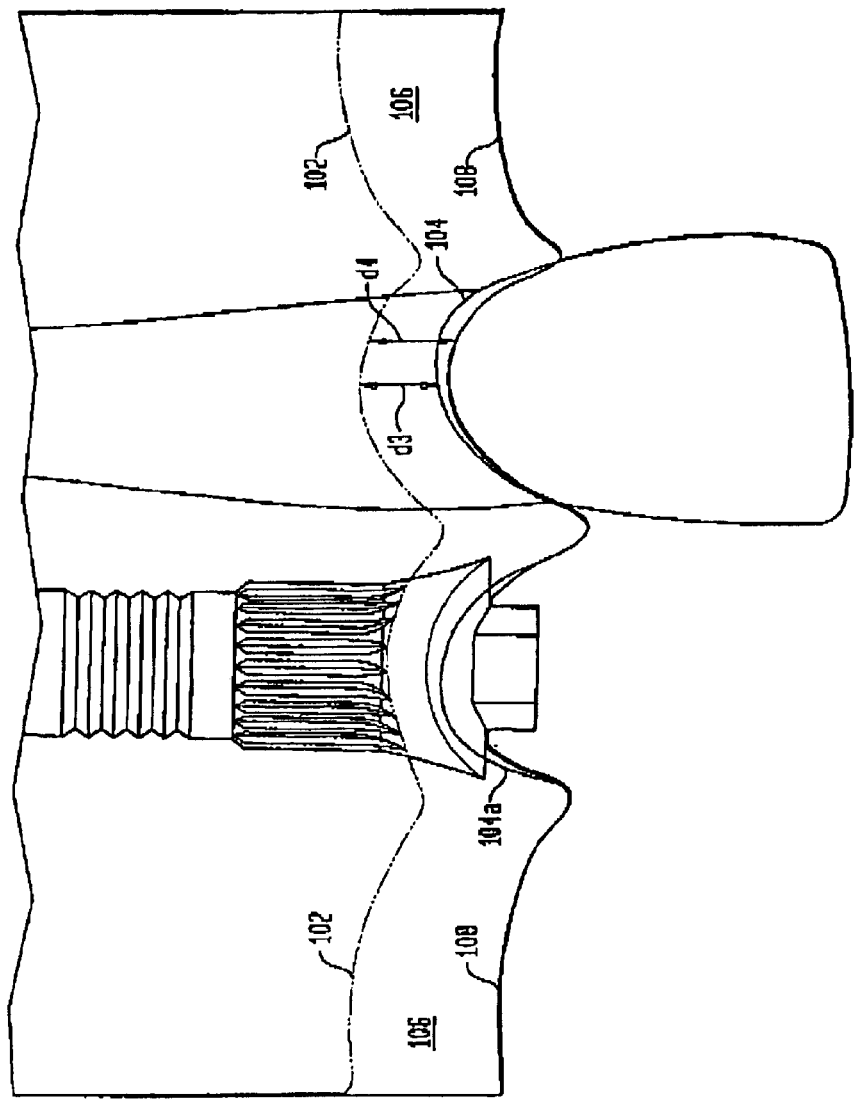
FIG. 8 is a front view of the upper jaw bone with the dental implant of the present invention positioned therein.

The distance "d1" from the terminus of the body portion 14 to the top surface 28 is preferably less at the buccal side of the implant and rises toward the interproximal side of the implant, as shown in FIG. 2. More preferably, the surface contour of the top surface substantially matches the shape of the cemento-enamel junction of the tooth being replaced, at least from the mid-buccal portion to the mid-interproximal portion of the implant 10, as shown in FIG. 8.

Returning to FIGS. 2 and 3, as mentioned above, it is preferred that the longitudinal grooves 20 extend into the head portion 12 of the dental implant 10. During implantation, described further below, it is preferred that the ends of the longitudinal grooves be positioned at or slightly below the bone crest, to help maintain natural bone morphology during healing. The ends of the longitudinal grooves 20 can be up to about 0.5 mm below the bone crest to obtain this advantage. In addition, the top of the longitudinal grooves 20 in this embodiment provide a reference position for the practitioner to know when the implant has been sufficiently inserted. In the insertion of prior art implants, it is difficult to precisely position the implant, resulting in penetration of the sinus cavities.

The distance "d2" between the end of each groove 20 within the head portion 12 and the top surface 28 of the implant 10 is preferably constant. For a typical implant, 1.80 mm, which is the natural distance from the crest 102 of the jawbone to the cemento-enamel junction 104 in an adult tooth, is the preferred distance d2. (See FIGS. 2 and 3). The top surface 28 of the implant is then positioned approximately at the location of cemento-enamel junction of the tooth being replaced.

Figure 5A:
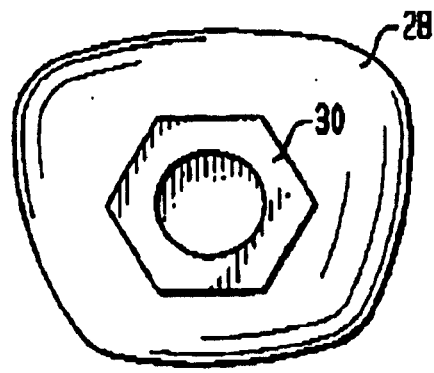
FIGS. 5a–5c are plan views of the top surfaces of the dental implants of showing preferred shapes for supporting a molar, a premolar and an anterior incisor, respectively.
Figure 5B:
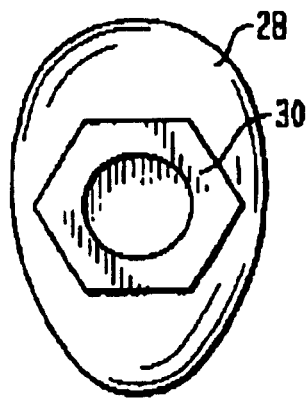
Figure 5C:
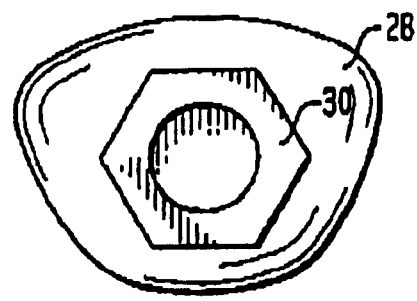

The shape of the circumference of the top surface 28 of the head portion 12 also preferably substantially matches the circumference of a cross-section the natural tooth at the cemento-enamel junction of the natural tooth. FIGS. 5a, 5b and 5c, are plan views of the top surfaces 28 of three head portions of three dental implants, showing the preferred shapes for supporting a molar, a premolar and an incisor, respectively.

Returning to FIGS. 2 and 3, the tip portion 16 of the implant 10 preferably includes a hole 32 extending therethrough. Preferably, the hole 32 extends completely through the tip portion 16, but that is not required. The surface of the tip portion 16 is preferably roughened. The tip portion preferably has a slight inward taper from the end of the body portion to the tip 17 of the implant 10, as shown in FIGS. 2 and 3.

The dental implant 10 is preferably made of titanium in accordance with known manufacturing techniques. Other biocompatible materials used as dental implants may be used, as well.

FIGS. 4a and 4b are side views of an alternative configuration of a dental implant 10a, wherein the longitudinal grooves 20 do not extend into the head portion. Instead, a lower portion of the head portion 12a, below line X in the implant 10a, is surface treated by acid etching, sand blasting with large grit and acid etching ("SLA"), titanium plasma sprayed ("TPS") or blasted with hydroxyapetite ("HA"), as is known in the art, to improve bone integration with the implant 10. As above, the upper portion of the head 12b, above line X in FIGS. 4a and 4b, is preferably polished to provide a smooth surface which inhibits the collection of bacteria. The interface between the upper portion of the head 12b and the lower portion 12a is preferably positioned at or slightly below the bone crest and provides a reference position for placement of the dental implant 10a. The distance from line X to the top surface 28 is also preferably a constant 1.80 mm. The remainder of the implant 10a is the same as the implant 10 in FIGS. 2 and 3.

FIGS. 6a–6h are a series of saggital cross-sectional views of the upper jaw 50 of a patient, illustrating a method of inserting the dental implant 10 into the upper jawbone, in accordance with the present invention. The gums 52, an outer layer of cortical bone 54a, an inner layer of the cortical bone 54b, a portion of trabecular bone 56 and a sinus cavity 58 are shown.

Figure 6A:
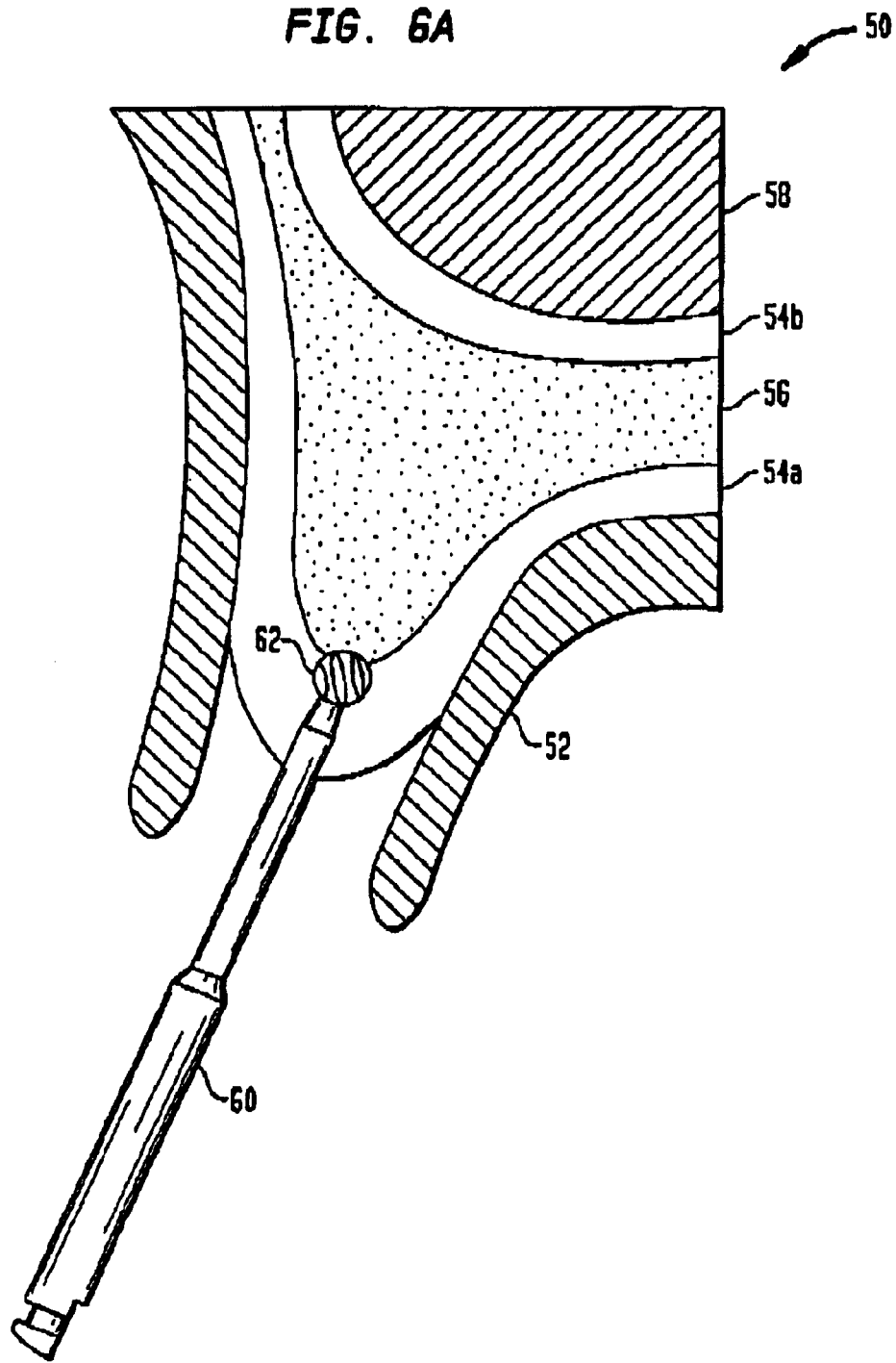
FIGS. 6a–6f are a series of saggital cross-sectional views of the upper jaw, illustrating a method of inserting the dental implant of FIG. 1 into the upper jawbone in accordance with the present invention.
Figure 6B:
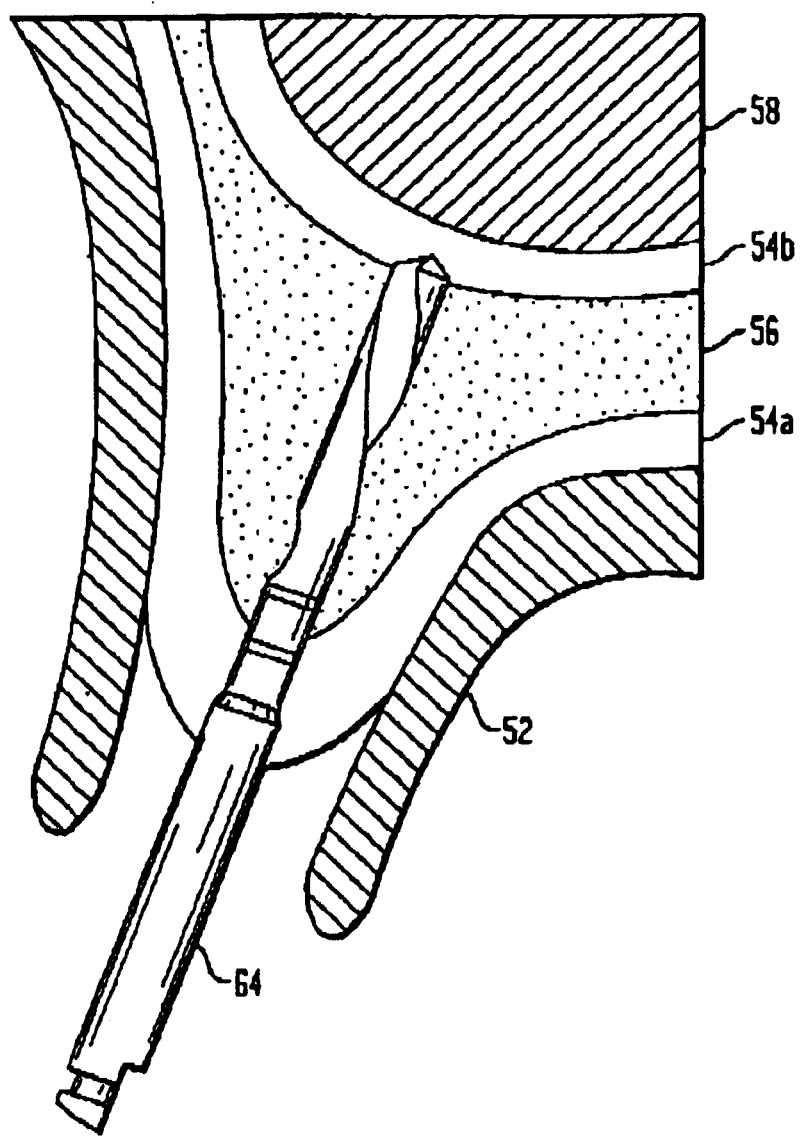
Figure 6C:
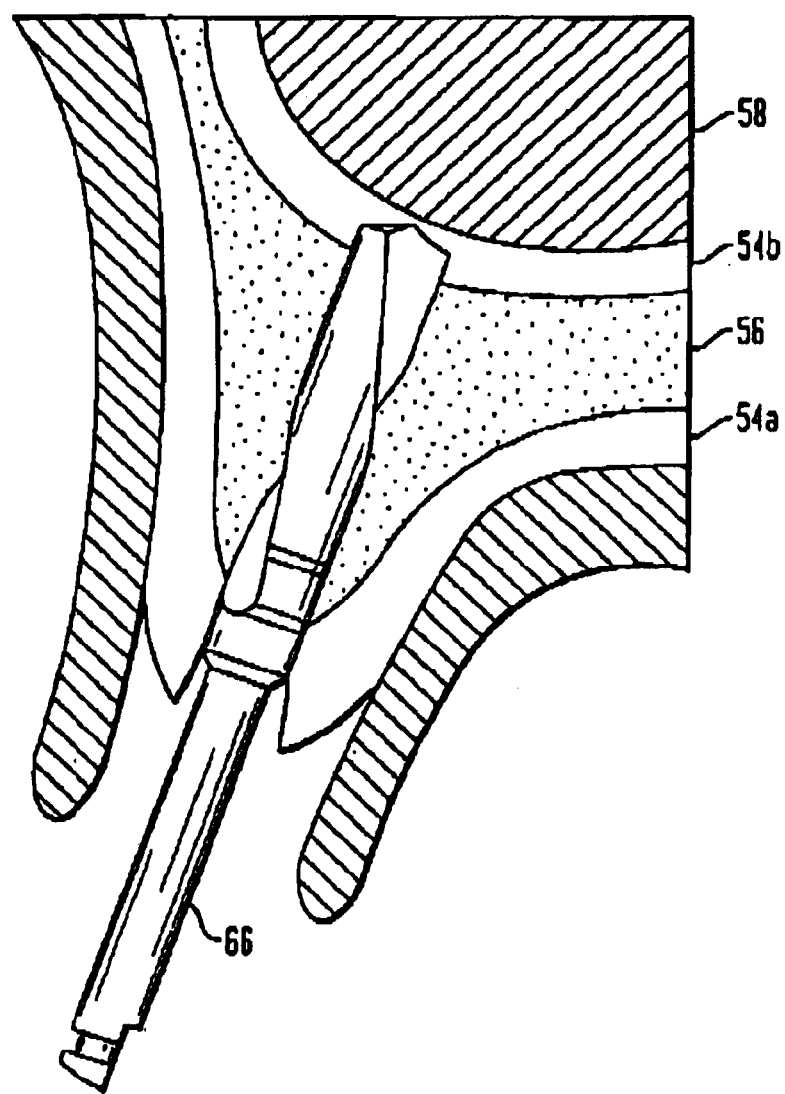

An implant drill with a round tip is used to penetrate the outer layer of cortical bone 54a, as shown in FIG. 6a. A 2 mm twist drill 60 is then used to penetrate through the trabecular bone 56, to the inner layer of cortical bone 54b, as shown in FIG. 6b, forming an opening. A 3 mm twist drill 66 is then used to widen the opening created by the 2 mm twist drill 64, as shown in FIG. 6c.

Figure 6D:
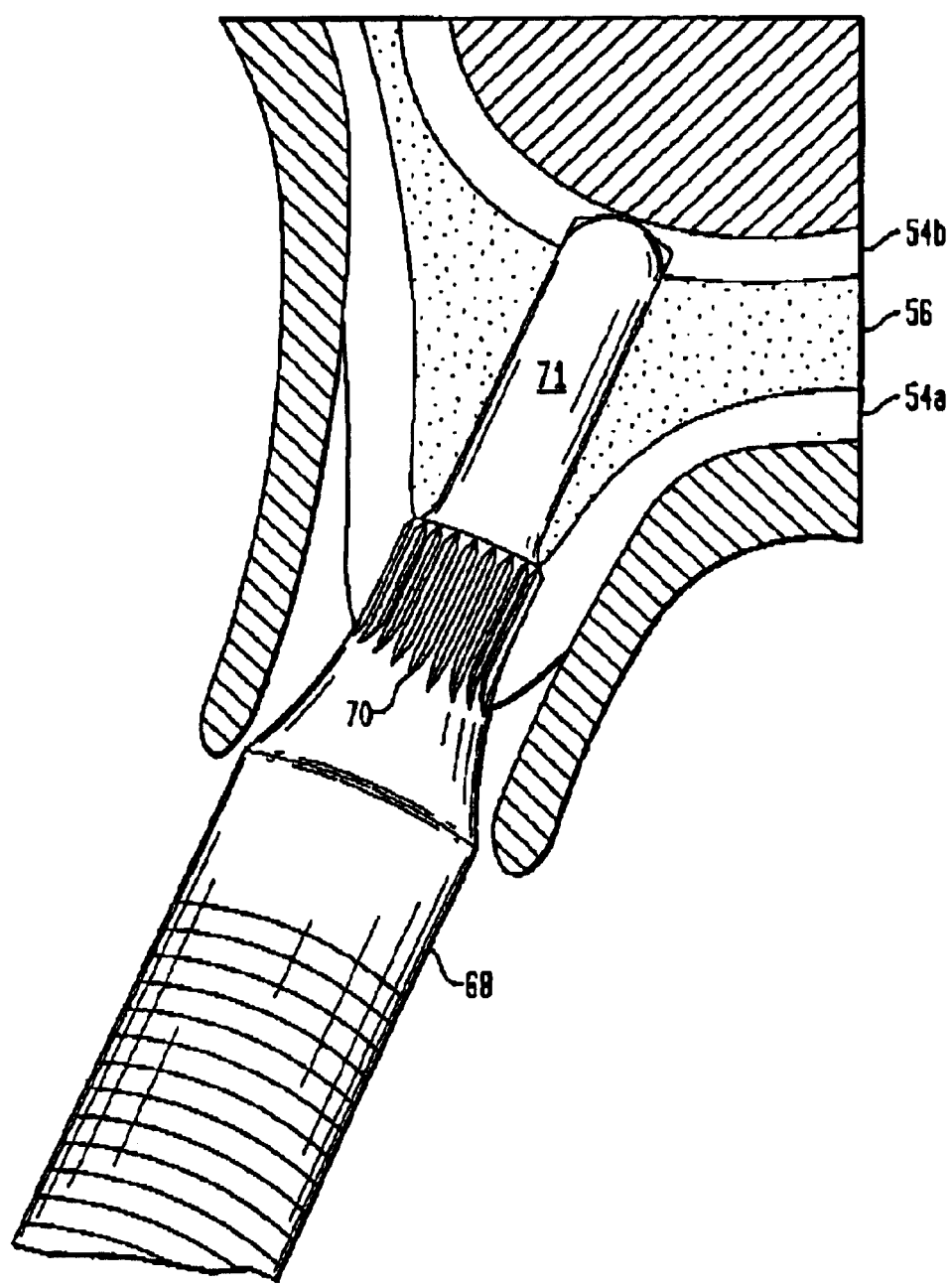
Figure 7A:
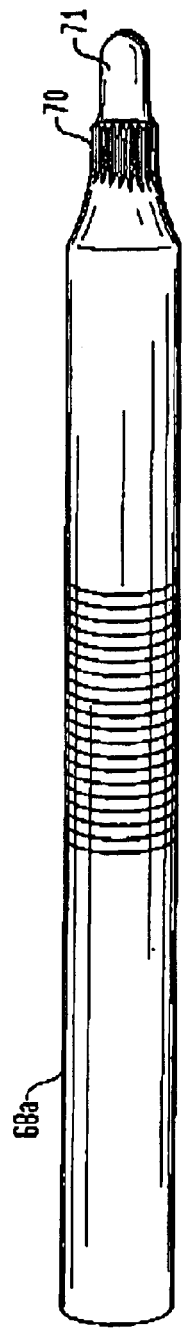
FIG. 7a and FIG. 7b are side views of osteotomes for use in the process of the present invention.
Figure 7B:
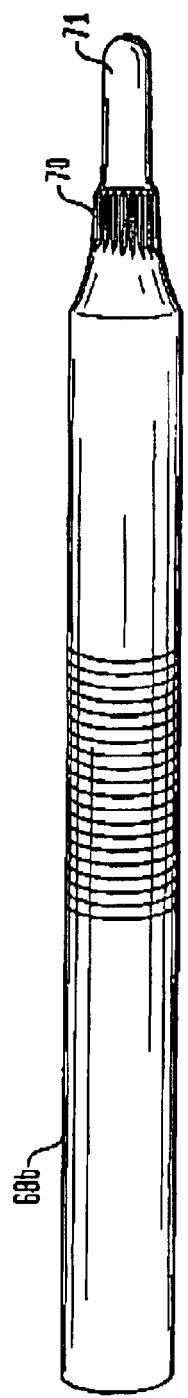

A profiling instrument, or osteotome 68, is then used to shape the opening, as shown in FIG. 6d. Two osteotomes 68a, 68b are shown in FIGS. 7a and 7b, as well. The osteotome 68a is for the implantation of dental implants for supporting molar type prosthetic teeth. The osteotome 68b is for the implantation of dental implants for supporting anterior and pre-molar type prosthetic teeth. The osteotomes 68a and 68b include a body portion with longitudinal grooves 70 substantially matching the longitudinal grooves 20 of the dental implant 10 to be inserted into the opening. The outer diameter and the depth of the longitudinal grooves 70 of the osteotome 68a, 68b are slightly smaller than that of the longitudinal grooves 20 of the dental implant 10, so that the implant will fit tightly in the opening, improving primary stability. The depth of the grooves 70 is preferably about 1 mm. The portion 71 of the osteotome 68 between the grooves 70 and the tip of the osteotome is preferably smooth. The outer diameter of the portion 71 is also preferably slightly smaller than the outer diameter of the second section 22 and the tip portion 16 of the dental implant 10. The longitudinal grooves 70 of the osteotomes 68a, 68b can have an outer diameter of from about 3.15 mm to about 6.0 mm, for example, depending on the tooth being replaced.

Figure 6E:
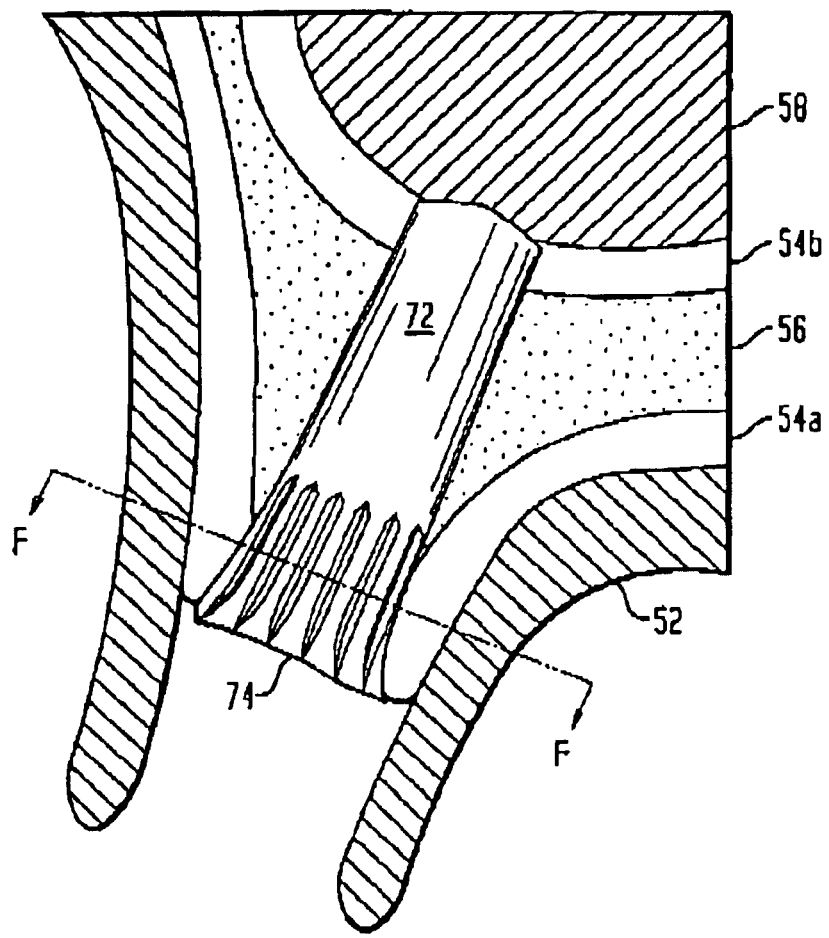

FIG. 6e is a side view of the opening 72 shaped by the osteotome 68. The osteotome 68 atraumatically forms a plurality of grooves 74 in the trabecular bone 56 and outer layer cortical bone 54a, substantially in the direction of the longitudinal axis of the opening 72.

Figure 6F:
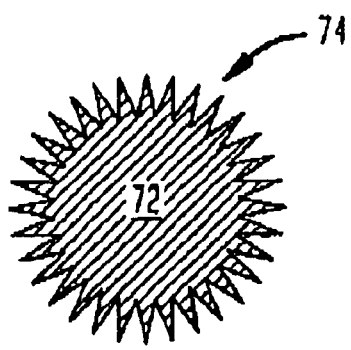

FIG. 6f is a cross-sectional view of the opening 72 along line f—f of FIG. 4e, showing the longitudinal grooves 74.

A dental implant 10 is preferably chosen having a length such that when inserted, the apical tip 76 of the dental implant 10 contacts the inner surface of the inner cortical bone 54b and the ends of the longitudinal grooves 20 in the head portion 12 are at the level of the crest 102 of the cortical bone 54a, or slightly below the crest 102, as shown in FIG. 8g. In FIG. 9, which is a front view of upper jaw, a natural tooth 100 is shown adjacent to the extracted tooth, the cemento-enamel junction 104 of the natural tooth 100, the gingivus 106 and the gingival margin 108 are also indicated.

To insert the dental implant 10, the implant 10 is oriented such that the buccal side of the implant faces the buccal side of the jaw and the lingual side of the implant 10 faces the lingual side of the jaw. During insertion of the dental implant 10, the longitudinal grooves 20 of the dental implant 10 are aligned with the longitudinal grooves 70 formed in the wall of the opening 72, preventing rotation of the implant 10 after placement in the opening 72. Since the outer diameter of the horizontal thread 24 or grooves of the dental implant 10 is less than the outer diameter of the longitudinal grooves 74 formed in the opening 72, the horizontal threads 24 of the dental implant 10 pass through the opening 72 unimpeded. The implant 10 is inserted into the opening 72 until the ends of the longitudinal grooves 20 in the head portion are aligned with or slightly below the bone crest 102. The ends of the grooves 20 are preferably not more than 0.5 mm below the bone crest.

Figure 6G:
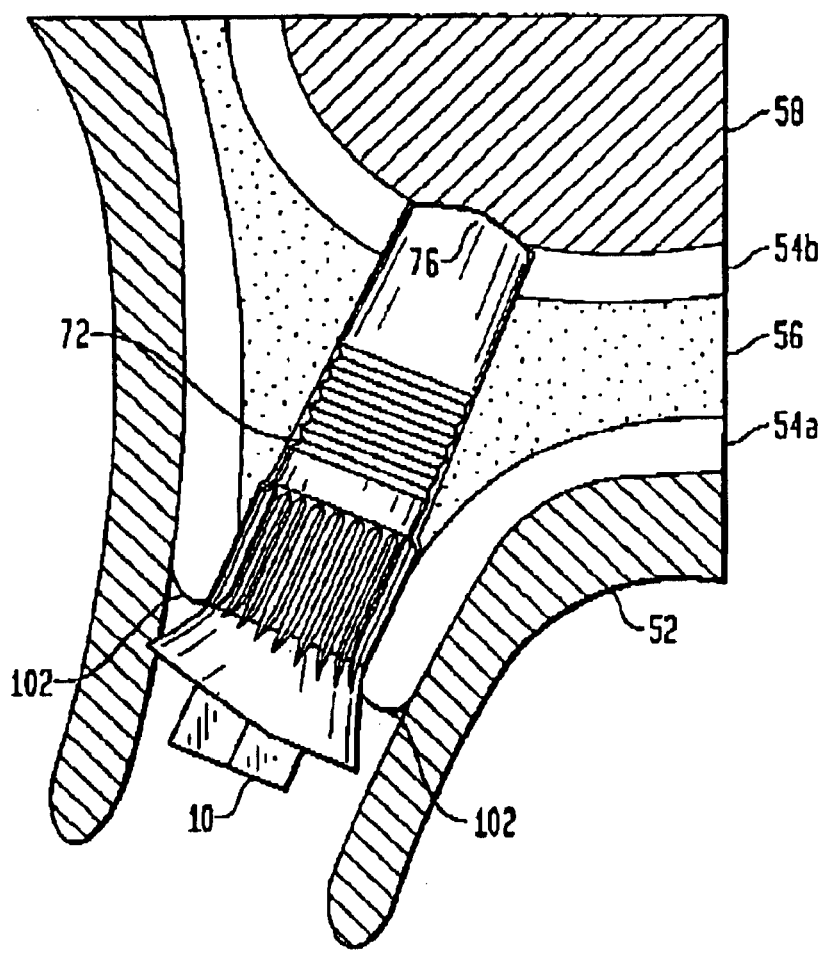

FIGS. 6g and 8 show the dental implant within the opening 72. The longitudinal grooves 74 of the opening 72 provide primary stability for the implant 10 and properly align the head of the implant in the mid-buccal portion of the osteotomy. Positioning the ends of the longitudinal grooves 20 at or near the bone crest 102 locates the top surface 28 of the implant 10 at or near the cemento-enamel junction 104a of the tooth being replaced. The contour of the the top surface 28 of the head portion 12 from the mid-buccal to mid-interproximal portions of the implant, generally follows the shape of the cemento-enamel junction 104, 104a, the bone crest 102 and the gingival margin 108. The shape of the side wall of the head portion 14 also substantially matches the shape of the outer surface of the cervical ⅓ of the root of the natural tooth being replaced. These conditions contribute to minimizing adverse immunological responses.

After implantation, bone grows into the recesses of the horizontal thread 24 or grooves, as well as the longitudinal grooves 20, securing the dental implant 10 in position in the jaw bone. The longitudinal grooves 20 continue to prevent rotation of the implant 10 while the horizontal grooves 24 prevent the dental implant from being pulled out. As the bone grows into the opening 32 in the tip portion 16, it is further secured against pull-out. The surface treatments also contribute to osteointegration.

Figure 6H:
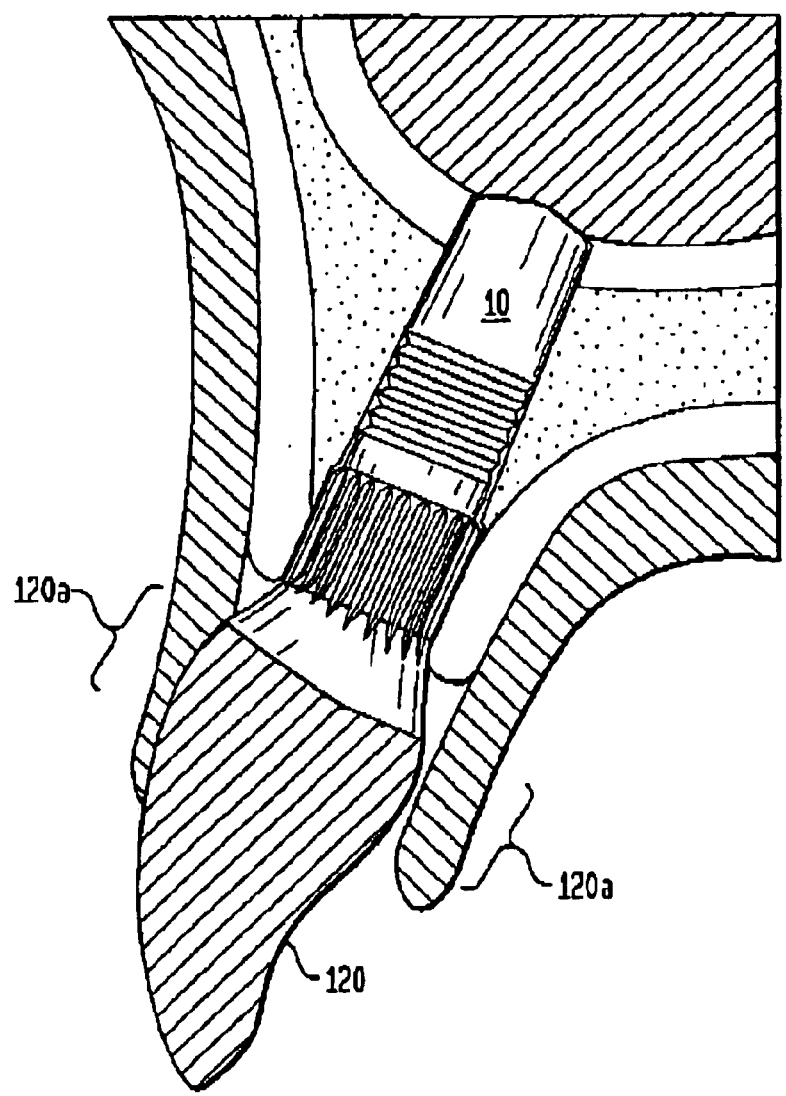

After sufficient time for the implant to become integrated with the bone, a prosthetic tooth 120 is attached to the implant, as shown in FIG. 6h. Since the head portion 12 matches the shape of the natural tooth and the top surface 28 of the head portion 12 extends above the bone crest 102, an abutment is not be required. However, an abutment may be used if desired. Use of an abutment does not provoke an adverse immunological response in the bone since the top surface of the implant 10 is above the bone crest 102.

Preferably, the shape of the portion 120a of the prosthetic tooth 120 corresponding to the cervical ⅓ of the crown of the tooth being replaced substantially matches the shape of the cervical ⅓ of that tooth, minimizing pockets between the prosthetic tooth and the gingivus. The remainder of the prosthetic tooth can also now more closely match the shape of the natural tooth being replaced. The shape of the cervical ⅓ of the tooth being replaced may be determined by taking an impression of the natural tooth, as is known in the art. If there is no natural tooth, then the optimum shape of the prosthetic tooth may be approximated by analysis of adjacent teeth and the height and width of the patient's face, as is known in the art. Since the shape of the head portion 12 of the dental implant 10 of the invention more closely matches the shape of the cervical ⅓ of the root of the tooth being replaced, the prosthetic tooth 120 can more closely match the shape of the cervical ⅓ of the tooth being replaced. The transition between the dental implant and the prosthetic tooth is more smooth than with dental implants of the prior art, also decreasing the presence of pockets between the prosthetic tooth and the gingivus.

The outwardly flaring head portion 12 of the dental implant 10 closes the orifice of the opening 72 in the jawbone, preventing soft tissue penetration and improving bone regeneration. Gaps below the bone line, where soft tissue cannot enter, will be filled with bone as the bone grows around the implant 10. Voids do not develop which can collect food or plaque, or provide space for the growth of soft tissue. In addition, since the cross-sectional shape of the head portion 12 of the implant 10 generally matches the corresponding cervical ⅓ of the root and cervical ⅓ of the crown of the natural tooth being replaced, gaps which could develop at the bone line into which soft tissue can grow are minimized.

As discussed above, the distance d3 from the crest 102 of the jawbone to the cemento-enamel junction 104 in an natural adult tooth is typically about 1.80 mm and the distance d4 from the crest 102 to the gingival margin in an adult tooth is typically about 3 mm. The implant system including the dental implant 10 and the prosthetic tooth preferably approximates these natural conditions, minimizing adverse immunological responses by the bone to the implant.

It is noted that the actual cemento-enamel junction drops slightly from the midpoint of the interproximal surface of the tooth toward the lingual side of the tooth. That portion of the junction is preferably not matched by the dental implant 10, to ease manufacturability and clinical application. Since the top surface of the head portion 12 of the implant 10 is above the bone crest 102 and the majority of the top surface of the head portion 12 (from the mid-buccal to mid-interproximal portion) matches the shape of the cemento-enamel junction, there should not be significant bone resorbtion and resulting recession of the gingival margin. Even if there is some bone resorbtion and gingivus recession, however, it is at the rear of the tooth, which cannot be seen.

If desired, however, the lingual portion of the top surface of the implant could also follow the lingual portion of the cemento-enamel junction of the tooth being replaced. FIG. 9 is a plan view of the proximal side of such an implant 10b, wherein the height d1 of the head portion 12 of the implant, from the body portion 14 to the top surface 28, increases from the buccal portion B of the implant 10a, to the interproximal portion I, and the decreases from the interproximal portion I to the longitudinal portion of the implant, as does the cemento-enamel junction of a natural tooth. The height d1 of the buccal portion is substantially the same as the height d1 of the lingual portion. The distance d2 from the ends of the longitudinal grooves 20 in the head portion 14 to the top surface 28 is also preferably maintained constant, at about 1.80 mm. The remainder of the implant 10b is the same as implant 10 in FIGS. 2 and 3.

Figure 10A:
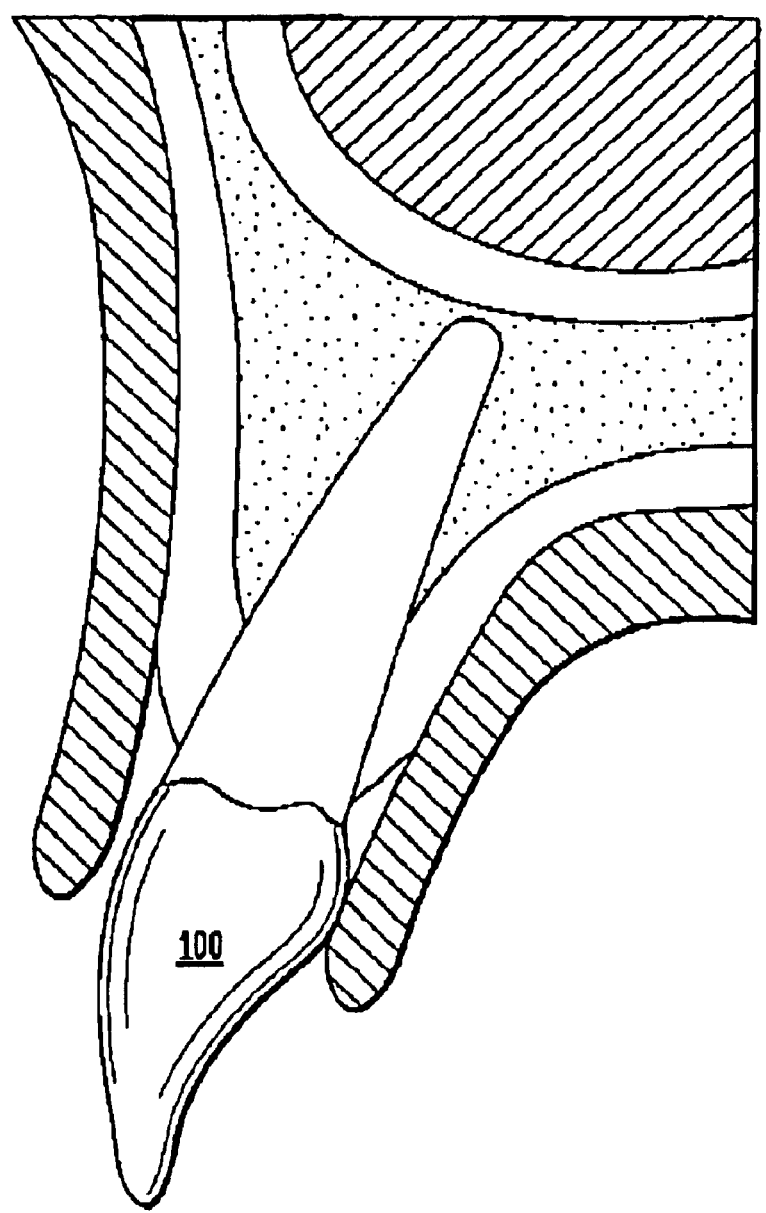
FIGS. 10a–10c illustrate various steps in the method of inserting the dental implant in the upper jawbone to replace a tooth to be extracted in accordance with the present invention.
Figure 10B:
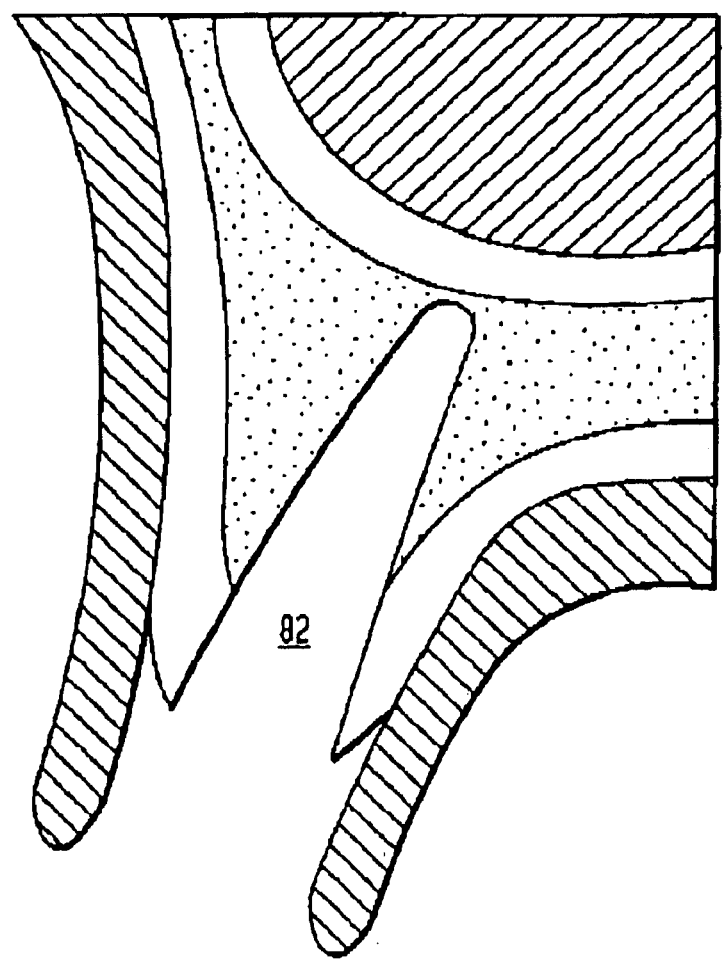
Figure 10C:
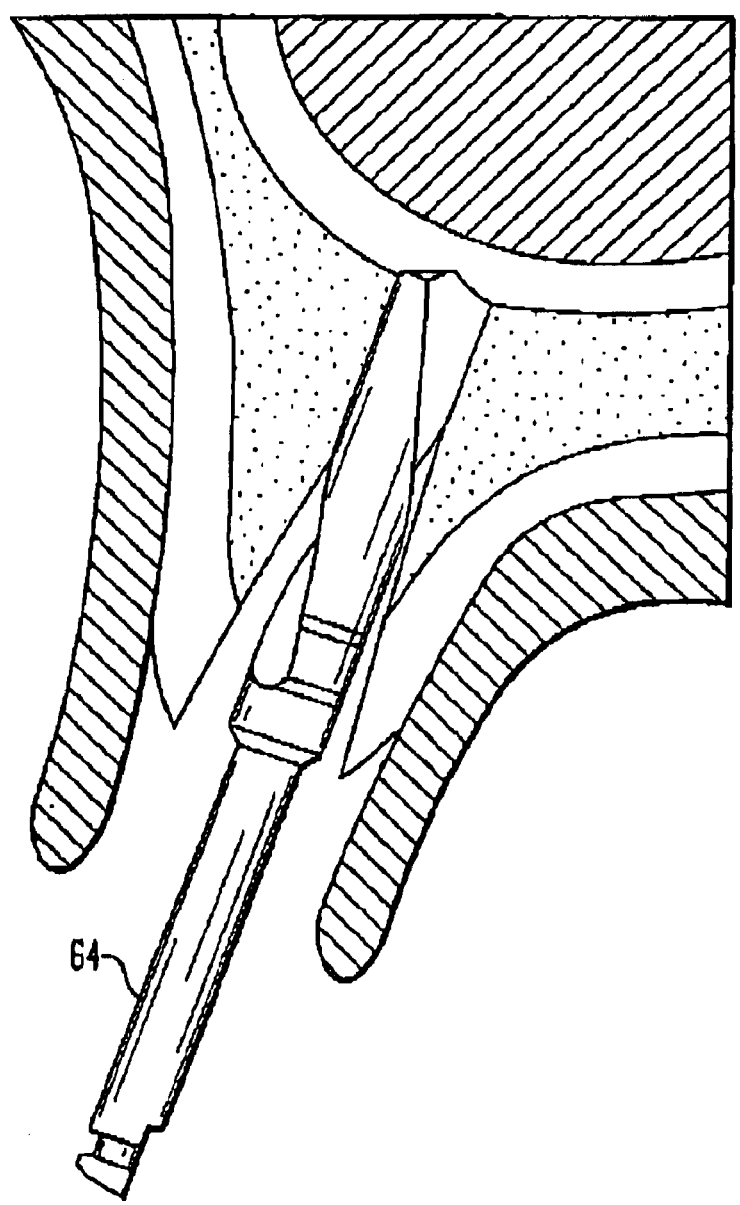

FIGS. 10a–10c illustrate various steps in the method of inserting the dental implant 10 of the present invention to replace a tooth 100 to be extracted. FIG. 10a shows a tooth 100 to be extracted by an a traumatic technique which minimizes damage to the bone, as is known in the art. Before extraction, the mesial-distal (MD) and buccal-lingual (BL) dimensions of the tooth are measured. A properly sized implant is then selected. FIG. 10b shows the opening 82 left by the extracted tooth. A 3 mm twist drill 64 is then used to widen the hole left by the tooth 100, as shown in FIG. 10c. The osteotome 68a, 68b is then used and the dental implant 10 is inserted, as described above with respect to FIGS. 6d–6g.

FIGS. 11a and 11b show another configuration of a dental implant 10b in accordance with the present invention, wherein the head portion 12' is surface treated, as described above with respect to the dental implant 10a shown in FIGS. 4a and 4b. The head portion 12' has a greater length, as measured from the terminus of the body portion 14' to the top surface 28' of the head portion 12', than in the dental implant 10a of FIGS. 4a and 4b. The body portion 14' and in particular the longitudinal grooves 20', are correspondingly shorter. As in the configuration of FIGS. 4a and 4b, the upper portion 12b' is polished and the interface X' between the upper portion 12b 'and the lower portion 12a 'serves as a reference line for positioning of the implant with respect to the bone crest. In this configuration, the distance d1' from the terminus of the body portion 14' to the top surface 28' of the head portion 12' is less at the mid-buccal portion of the implant 10b, rises toward the mid-interproximal proximal portion of the implant and then decreases toward the mid-lingual portion of the implant. As above, it is not necessary for that distance to decrease from the mid-interproximal to the mid-lingual portion of the implant.

It is noted that due to natural asymmetries between the right and left sides of certain types of natural teeth, it may be impractical with current manufacturing and implantation methods to exactly match the cemento-enamel junction, even at the buccal portion of a tooth. It is not necessary for the implant of the present invention to match the right-left asymmetries of cemento-enamel junction of a natural tooth, to achieve the advantages of the present invention. However, if the implant is custom designed for a particular tooth and such asymmetry is matched, even better results may be obtained.

While the dental implants and prosthetic teeth of the present invention have been discussed with respect to implantation in the upper jaw, such implants and prosthetic teeth may be used in the lower jaw, as well.

While preferred embodiments for practicing the present invention have been described above, it is understood that modifications may be made from these preferred embodiments without departing from the scope of the present invention, which is defined by the following claims.

I claim:

1. A one-piece dental implant having a longitudinal axis, comprising:

a head portion at a first end of the implant;

a tip portion at a second end of the implant; and a body portion between the head portion and the tip portion, the body portion having a first portion proximate the head portion with a plurality of longitudinal grooves substantially parallel to the longitudinal axis and a second portion proximate the tip portion having a substantially circumferential groove, wherein the outer diameter of the first portion is greater than the outer diameter of the second portion, the fast and second portion for being embedded in a jaw bone, and wherein at least a portion of the contour of a top surface of the head portion substantially matches the shape of the cemento-enamel junction of a tooth being replaced.

2. The dental implant of claim 1, wherein the circumferential groove is a spiral thread.

3. The dental implant of claim 1, comprising a plurality of substantially parallel, circumferential grooves substantially perpendicular to the longitudinal axis of the implant.

4. The dental implant of claim 1, wherein the longitudinal gooves extend into the head portion.

5. The dental implant of claim 1, wherein the implant has a buccal side for being aligned with a buccal side of the jaw bone and a lingual side for being aligned with a lingual side of the jaw bone, and wherein the height of the implant is smaller on the buccal side and rises interproximally toward the lingual side.

6. The dental implant of claim 1, wherein the tip portion defines a hole therethrough, the hole substantially perpendicular to the longitudinal axis.

7. The dental implant of claim 1, wherein the circumference of a the top surface of the head portion substantially matches the shape of the circumference of the tooth being, replaced, proximate the cemento-enamel junction of the tooth being replaced.

8. The dental implant of claim 1, further comprising a hex for direct attachment of a prosthetic tooth, the hex extending from the head portion.

9. The dental implant of claim 1, wherein the head portion of said implant has a side wall having a shape substantially matching the shape of the cervical ⅓ of the root of the tooth being replaced.

10. The dental implant of claim 1, wherein the top surface of the head portion has a surface contour substantially following the shape of the cemento-enamel junction of the tooth being replaced at least at the portions of the implant corresponding to the buccal and interproximal portions of the implant.

11. The dental implant of claim 1, wherein the top surface of the head portion has a surface contour substantially following the shape of the cemento-enamel junction of the tooth being replaced at the lingual portion of the implant.

12. The dental implant of claim 1, wherein a portion of the side wall of the head portion proximate the body portion is surface treated.

13. A one-piece dental implant having a longitudinal axis, comprising:

a head portion at a first end of the implant;

a tip portion at a second end of the implant; and a body portion between the head portion and the tip portion, the body portion having a first portion proximate the head portion with at least one longitudinal groove substantially parallel to the longitudinal axis and a second portion proximate the tip portion having a substantially circumferential groove, wherein the outer diameter of the first portion is greater the outer diameter of the second portion, the first and second portion for being embedded in a jaw bone, and wherein at least a portion of the contour of a top surface of the head portion substantially matches the shape of the cemento-enamel junction of a tooth being replaced.

14. A dental implant for supporting an artificial tooth, the implant having a longitudinal axis, the implant comprising:

a head portion at a first end of the implant, the head portion having a top surface with a circumference substantially matching the circumference of a tooth to be replaced, proximate the cemento-enamel junction of the tooth being replaced, and wherein at least a portion of the contour of the top surface substantially matches the shape of the cemento-enamel junction of the tooth being replaced;

a tip portion at a second end of the implant; and a body portion between the head portion and the tip portion.

15. The dental implant of claim 14, wherein the top surface of the head portion of the implant has a surface contour substantially following the shape of the cemento-enamel junction of the tooth being replaced, at least from the mid-buccal to the mid-interproximal portions of the implant.

16. The dental implant of claim 15, wherein the surface contour of the top surface of the head portion further substantially follows the shape of the cemento-enamel junction at the lingual portion of the implant.

17. The dental implant of claim 15, wherein the body portion has a first portion proximate the head portion with at least one groove substantially parallel to the longitudinal axis and a second portion proximate the tip portion having a substantially circumferential groove, the outer diameter of the first portion being greater than the outer diameter of the second portion, the first and second portion for being embedded in the jaw bone.

18. A dental implant having a longitudinal axis, comprising:

a head portion at a first end of the implant;

a tip portion at a second end of the implant; and a body portion between the head portion and the tip portion;

wherein the dental implant has a buccal side for being aligned with a buccal side of the jaw bone and a lingual side for being aligned with a lingual side of the jaw bone, and interproximal sides between the buccal and lingual sides, the height of the implant being less at the buccal side of the implant and rising toward the interproximal sides of the implant, such that at least a portion of the contour of a top surface of the head portion substantially matches the shape of the cemento-enamel junction of a tooth being replaced.

19. The dental implant of claim 18, wherein the circumference of the top surface of the head portion substantially matches the shape of the circumference of the tooth being replaced, proximate the cement enamel junction of the tooth being replaced.

20. The dental implant of claim 18, wherein the height of implant decreases from the interproximal sides to the lingual side of the implant.

21. The dental implant of claim 18, wherein the body portion has a first portion proximate the head portion with at least one groove substantially parallel to the longitudinal axis and a second portion proximate the tip portion having a substantially circumferential groove, wherein the outer diameter of the first portion is greater than the outer diameter of the second portion.

22. The dental implant of claim 18, wherein a portion of the side wall of the head portion of the implant proximate the body portion, is surface treated.

23. A dental implant and prosthetic tooth system comprising:

a dental implant comprising a head portion, a tip portion and a body portion between the head portion and the tip portion, the head portion having a buccal side for being aligned with a buccal side of a jaw bone, a lingual side for being aligned with a lingual side of the jaw bone and interproximal sides between the buccal and lingual sides, the height of the implant being less on the buccal side and rising toward the interproximal sides, such that at least a portion of the contour of a top surface of the head portion substantially matches the shape of the cemento enamel junction of a tooth being replaced; and a prosthetic tooth for being attached to the head portion, the prosthetic tooth having a portion having a shape substantially matching the shape of the cervical ⅓ of the crown of the tooth being replaced.

24. The system of claim 23, wherein the head portion of the implant has a side wall with a shape substantially matching the shape of the cervical ⅓ of the root of the tooth being replaced.

25. The system of claim 24, wherein the head portion has a top surface wiih a circumference qubstanltially matching the circumference of the tooth being replaced, at the cementoenamel junction of the tooth being replaced.

26. The system of claim 23, wherein the body portion has a fust portion proximate the head portion with at least one longitudinal groove substantially parallel to the longitudinal axis and a second portion proxinmate the tip portion having a substantially circumferential groove, the outer diameter of th first portion being greater than the outer diameter of the second portion.

27. A dental implant and prosthetic tooth system, comprising:

a dental implant comprising a head porion, a tip portion and a body portion between the head portion and the tip portion, the head portion having a top surface with a circumference substantially matching the circumference proximate the cemento-enamel junction of a tooth being replaced and a contour at least partially matching the shape of the cemento-enamel junction of the tooth being replaced; and a prosthetic tooth for being attached to the top surface of the implant, wherein a portion of the prosthetic tooth has a shape substantially matching the shape of the cervical ⅓ of the crown of the tooth being replaced.

28. The system of claim 27, wherein the height of the top portion of the dental implant is less on the buccal side of the implant and rises toward the interproximal sides of the implant.

29. The system of claim 28, wherein the top portion of the implant has a side wall with a shape substantially matching the shape of the cervical ⅓ of the root of the tooth being replaced.

30. A one-piece, press-fit dental implant having a longitudinal axis, the dental implant comprising:

a head portion defining a circumferential surface and a top surface;

a tip portion defining a circumferential surface and a bottom surface; and a body portion between the head portion and the tip portion; the body portion defining a circumferential surface, wherein the circumferential surface of the head portion has a smooth surface with length along the longitudinal axis such that at least a portion of the contour of the top surface and the smooth surface substantially follow the shape of the cemento-enamel junction of a tooth that is to be replaced.

31. The dental implant of claim 30, wherein the length of the smooth surface of the head portion along the longitudinal axis is approximately the biological width.

32. The dental implant of claim 30, wherein the length of the smooth surface of the head portion along the longitudinal axis that is approximately 1.8 mm.

33. The dental implant of claim 30, wherein the head portion has length along the longitudinal axis such that an edge between the circumferential surface and the top surface of the head portion substantially follows the shape of the cemento-enamel junction of the tooth that is to be replaced, at least at portions of the dental implant corresponding to a buccal portion and an interproximal portion of the dental implant.

34. The dental implant of claim 30, wherein the top surface of the head has a surface contour that substantially follows the shape of the cemento-enamel junction of the tooth that is to be replaced, at least at the portions of the head portion corresponding to at least one of a buccal portion and an interproximal portion of the dental implant.

35. The dental implant of claim 30, wherein the shape of the circumferential surface of the head portion proximate an edge between the circumferential surface and the top surface of the head portion substantially matches the shape of the circumferential surface of the tooth that is to be replaced.

36. The dental implant of claim 30, wherein the circumferential surface of the head portion has a shape substantially matching the shape of the cervical 1/3 of the root of the tooth that is to be replaced.

37. The dental implant of claim 30, wherein the dental implant has a buccal side for being aligned with a buccal side of a jaw bone and a lingual side for being aligned with a lingual side of the jaw bone, wherein the head portion has a first length along the longitudinal axis on the buccal side and a second length along the longitudinal axis on the lingual side, the first length smaller than the second length.

38. The dental implant of claim 30, wherein the head portion further include a means for direct attachment of a prosthetic tooth.

39. The dental implant of claim 30, wherein the circumferential surface of the head portion further includes a surface treated portion proximate the body portion.

40. The dental implant of claim 30, wherein the circumferential surface of the body portion includes:
a longitudinal groove substantially parallel to the longitudinal axis, a spiral thread or a substantially circumferential groove substantially perpendicular to the longitudinal axis.

41. The dental implant of claim 30, wherein the body portion includes:
a first portion proximate the head portion, the first portion having a first diameter and a longitudinal groove substantially parallel to the longitudinal axis; and
a second portion proximate the tip portion, the second portion having a second diameter and a substantially circumferential groove, wherein the first diameter is greater than the second diameter.

42. The dental implant of claim 30, wherein the body portion includes:
a plurality of longitudinal grooves, the longitudinal plurality of grooves extending into the head portion.

43. The dental implant of claim 30, wherein the tip portion defines a hole therethrough, the hole substantially perpendicular to the longitudinal axis.

44. A one-piece dental implant having a longitudinal axis, the dental implant comprising:
a head portion defining a circumferential surface and a top surface and including a means for direct attachment of a prosthetic tooth, at least a portion of the contour of the top surface substantially matching the shape of the cemento-enamel junction of a tooth that is to be replaced;
a tip portion defining a circumferential surface and a bottom surface; and
a body portion between the head portion and the tip portion; the body portion defining a circumferential surface;
wherein the circumferential surface of the head portion has a smooth surface with a length along the longitudinal axis that is approximately the biological width, a contour of the smooth surface perpendicular to the longitudinal axis substantially following the shape of the cemento-enamel junction of the tooth that is to be replaced, the circumferential surface of the head portion having a shape with
a first portion proximate an edge between the circumferential surface and the top surface of the head portion that substantially matches the shape of the circumferential surface of the tooth that is to be replaced; and
a second portion that substantially matches the shape of the cervical 1/3 of the root of the tooth that is to be replaced.

45. The dental implant of claim 44, wherein the circumferential surface of the head portion further includes a surface treated portion proximate the body portion.

46. The dental implant of claim 44, wherein the circumferential surface of the body portion includes:
a longitudinal groove substantially parallel to the longitudinal axis, a longitudinal groove substantially parallel to the longitudinal axis and extending into the head portion, a spiral thread, or a substantially circumferential groove substantially perpendicular to the longitudinal axis.

47. A one-piece, press-fit dental implant having a longitudinal axis, the dental implant comprising:
a head portion defining a circumferential surface and a top surface;
a tip portion defining, a circumferential surface and a bottom surface; and
a body portion between the head portion and the tip portion; the body portion defining a circumferential surface, wherein the circumferential surface of the head portion has a smooth surface with length along the longitudinal axis such that the smooth surface substantially follows the shape of the cemento-enamel junction of a tooth that is to be replaced, the body portion including a plurality of longitudinal grooves that extend into the head portion.

* * * * *

UNITED STATES PATENT AND TRADEMARK OFFICE
CERTIFICATE OF CORRECTION

PATENT NO. : 6,854,972 B1
DATED : February 15, 2005
INVENTOR(S) : Elian

It is certified that error appears in the above-identified patent and that said Letters Patent is hereby corrected as shown below:

Column 10,
Line 1, the term "fast" should read -- first --.
Line 24, after the term "being", delete the ",".

Column 12,
Line 16, the term "qubstanltially" should read -- substantially --.
Lines 17-18, the term "cementoenamel" should read -- cementoenamel --.
Line 20, the term "fust" should read -- first --.
Line 22, the term "proxinmate" should read -- proximate --.
Line 28, the term "porion" should read -- portion --.

Signed and Sealed this

Third Day of May, 2005

JON W. DUDAS
*Director of the United States Patent and Trademark Office*